(12) United States Patent
Glithero

(10) Patent No.: US 10,821,018 B2
(45) Date of Patent: Nov. 3, 2020

(54) DRAINAGE BAG SYSTEMS AND METHODS OF USING THE SAME

(71) Applicant: C.R. BARD, INC., Murray Hill, NJ (US)

(72) Inventor: Jason Iain Glithero, McDonough, GA (US)

(73) Assignee: C.R. BARD INC., Murray Hill, NJ (US)

( * ) Notice: Subject to any disclaimer, the term of this patent is extended or adjusted under 35 U.S.C. 154(b) by 778 days.

(21) Appl. No.: 15/526,232

(22) PCT Filed: Oct. 14, 2016

(86) PCT No.: PCT/US2016/057118
§ 371 (c)(1),
(2) Date: May 11, 2017

(87) PCT Pub. No.: WO2017/070019
PCT Pub. Date: Apr. 27, 2017

(65) Prior Publication Data
US 2017/0312114 A1    Nov. 2, 2017

Related U.S. Application Data (60) Provisional application No. 62/245,779, filed on Oct. 23, 2015.

(51) Int. Cl.
*A61F 5/44* (2006.01)
*A61F 5/451* (2006.01)
(Continued)

(52) U.S. Cl.
CPC ...... *A61F 5/4405* (2013.01); *A61B 5/150366* (2013.01); *A61B 10/007* (2013.01);
(Continued)

(58) Field of Classification Search
CPC .......... A61F 5/4405; A61F 5/44; A61F 5/451; A61B 5/150366; A61B 10/0038; A61B 10/007
(Continued)

(56) References Cited

U.S. PATENT DOCUMENTS 3,961,529 A    6/1976 Hanifl et al.
4,265,118 A *  5/1981 Griesel ................. A61F 5/4405
                                                73/427
(Continued)

OTHER PUBLICATIONS

International Search Report and Written Opinion from International Application No. PCT/US2016/057118 dated Jan. 10, 2017.

*Primary Examiner* — Andrew J Mensh
(74) *Attorney, Agent, or Firm* — Dorsey & Whitney LLP (57) ABSTRACT

Embodiments disclosed herein are directed to drainage bag systems configured to facilitate disposal of a fluid therein and methods of using the drainage bag systems. For example, the drainage bag systems may include a drainage container configured to receive and hold a fluid from a patient. The drainage container may be fluidly coupled and reversibly attached to a bag. The bag may be configured to selectively receive at least some of fluid held by the drainage container. The bag may be detached from the drainage container and disposed of in a substantially fluid tight manner without disrupting operation of the drainage container (e.g., receiving and holding a fluid).

19 Claims, 6 Drawing Sheets

(51) Int. Cl.
    *A61B 5/15* (2006.01)
    *A61B 10/00* (2006.01)
(52) U.S. Cl.
    CPC ............ *A61B 10/0038* (2013.01); *A61F 5/44* (2013.01); *A61F 5/451* (2013.01)
(58) Field of Classification Search
    USPC ........................................................ 604/323
    See application file for complete search history.

(56) References Cited

U.S. PATENT DOCUMENTS

| | | | |
|---|---|---|---|
| 4,319,573 A * | 3/1982 | Whitlock | A61F 5/4404 |
| | | | 604/323 |
| 4,533,354 A | 8/1985 | Jensen et al. | |
| 4,815,477 A * | 3/1989 | McWhorter | A61B 10/007 |
| | | | 251/4 |
| 5,919,146 A | 7/1999 | Propp | |
| 8,282,613 B2 | 10/2012 | Christensen | |
| 8,777,912 B2 | 7/2014 | Nishtala et al. | |
| 2003/0021736 A1* | 1/2003 | Kang | A61B 10/0096 |
| | | | 422/417 |
| 2007/0038143 A1* | 2/2007 | Christensen | A61B 5/036 |
| | | | 600/561 |
| 2014/0188061 A1* | 7/2014 | Locke | A61M 1/0049 |
| | | | 604/321 |

* cited by examiner

DRAINAGE BAG SYSTEMS AND METHODS OF USING THE SAME

CROSS-REFERENCE TO RELATED APPLICATIONS

This application claims priority to U.S. Provisional Application No. 62/245,779 filed on Oct. 23, 2015, the disclosure of which is incorporated herein, in its entirety, by this reference

BACKGROUND

Drainage bag systems typically include a single drainage bag. The drainage bag is fluidly coupled to a device, such as a Foley urinary catheter, which allows a fluid (e.g., urine, stool, blood, etc.) to flow into the drainage bag from a patient.

Fluid in the drainage bag may be removed therefrom by first detaching the drainage bag from the device, thereby preventing the device from draining additional fluid into the drainage bag. The fluid in the drainage bag may then be drained therefrom using a conventional collection bag outlet device formed in the drainage bag. The conventional collection bag outlet device may be configured to drain the fluid into a container or drain that is separate and distinct from the drainage bag. However, draining the fluid from the drainage bag may cause the fluid to splash and may contaminate the container.

Accordingly, manufacturers and users of drainage bag systems continue to seek improvements thereto.

SUMMARY

Embodiments disclosed herein are directed to drainage bag systems configured to facilitate disposal of a fluid therein and methods of using such drainage bag systems. For example, the drainage bag systems may include a drainage container configured to receive and hold a fluid from a patient. The drainage container may be fluidly coupled to and reversibly attached to a bag. The bag may be configured to selectively receive at least some of the fluid held by the drainage container. The bag may be detached from the drainage container and disposed of, for example, in a substantially fluid tight manner without disrupting operation of the drainage container (e.g., receiving and holding a fluid).

In an embodiment, a drainage bag system is disclosed. The drainage bag system includes a drainage container defining a first interior space configured to hold fluid therein. The drainage container further defines an outlet that allows access to the first interior space. The drainage bag system also includes a fluid dispensing device including a valve system that is configured to substantially prevent the fluid from flowing through the outlet when the fluid dispensing device is deactivated and permit the fluid to flow through the outlet when activated. The drainage bag system further includes a bag defining a second interior space configured to hold at least a portion of the fluid therein. The bag further defines an inlet. The inlet is positioned and configured to be selectively fluidly coupleable to the outlet of the drainage container such that at least a portion of the fluid in the drainage container can be dispensed into the bag when the fluid dispensing device is activated.

In an embodiment, a method of operating a drainage bag system is disclosed. The method includes filling at least a portion of a first interior space of a drainage container with a fluid. The method also includes selectively activating a fluid dispensing device operably coupled to the drainage container to permit the fluid to flow from the interior space through and out of an outlet of the drainage container. Finally, the method includes responsive to selectively activating the fluid dispensing device, filling at least a portion of a second interior space of a bag fluidly coupled to the drainage container with the fluid that flows through and out of the outlet of the drainage container.

In an embodiment, a drainage bag system is disclosed. The drainage bag system includes a drainage container defining a first interior space configured to hold fluid therein. The drainage container further defines an outlet that allows access to the first interior space. The drainage container includes a first attachment device. The drainage bag system also includes a fluid dispensing device including a valve system at least partially disposed within the first interior space. The valve system includes a piston configured to be moved from a first position to a second position. The piston substantially prevents the fluid from flowing through the outlet when in the first position and permits the fluid from flowing through the outlet when in the second position. The valve system also includes a manually-operable valve actuator operably coupled to the piston. The manually-operable valve actuator is configured to move the piston from the first position to the second position. The valve system further includes an elongated member extending from the piston to the manually-operable valve actuator. At least a portion of the elongated member is hollow. The elongated member further includes an inlet that fluidly couples the first interior space to the hollow portion of the elongated member. The hollow portion of the elongated member extends from the inlet of the elongated member to a portion of the outlet that is not in fluid communication with the piston. Finally, the drainage bag system includes a bag defining a second interior space configured to hold at least a portion of the fluid therein. The bag further defines an inlet. The inlet is positioned and configured to be selectively fluidly coupleable to the outlet of the drainage container such that at least a portion of the fluid in the drainage container can be dispensed into the bag when the fluid dispensing device is activated. The bag includes a second attachment device that is configured to be reversibly attached to the first attachment device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are directed to drainage bag systems configured to facilitate disposal of a fluid therein and methods of using such drainage bag systems. For example, the drainage bag systems may include a drainage container configured to receive and hold a fluid from a patient. The drainage container may be fluidly coupled to and reversibly attached to a bag. The bag may be configured to selectively receive at least some of the fluid held by the drainage container. The bag may be detached from the drainage container and disposed of, for example, in a substantially fluid tight manner without disrupting operation of the drainage container (e.g., receiving and holding a fluid).

The drainage bag systems disclosed herein may be configured to be used in any system that drains one or more fluids from a patient. For example, the drainage bag systems disclosed herein may be used in a urinary drainage system (e.g., a Foley catheter and drainage system). As such, the drainage bag systems disclosed herein may be configured to be a urinary drainage bag system. In other embodiments, the drainage bag systems disclosed herein may be used in a blood drainage system, a pleural drainage system, a peritoneal drainage system, a bowel drainage system (e.g., a stool collection bag), or another other suitable drainage system.

Figure 1A:
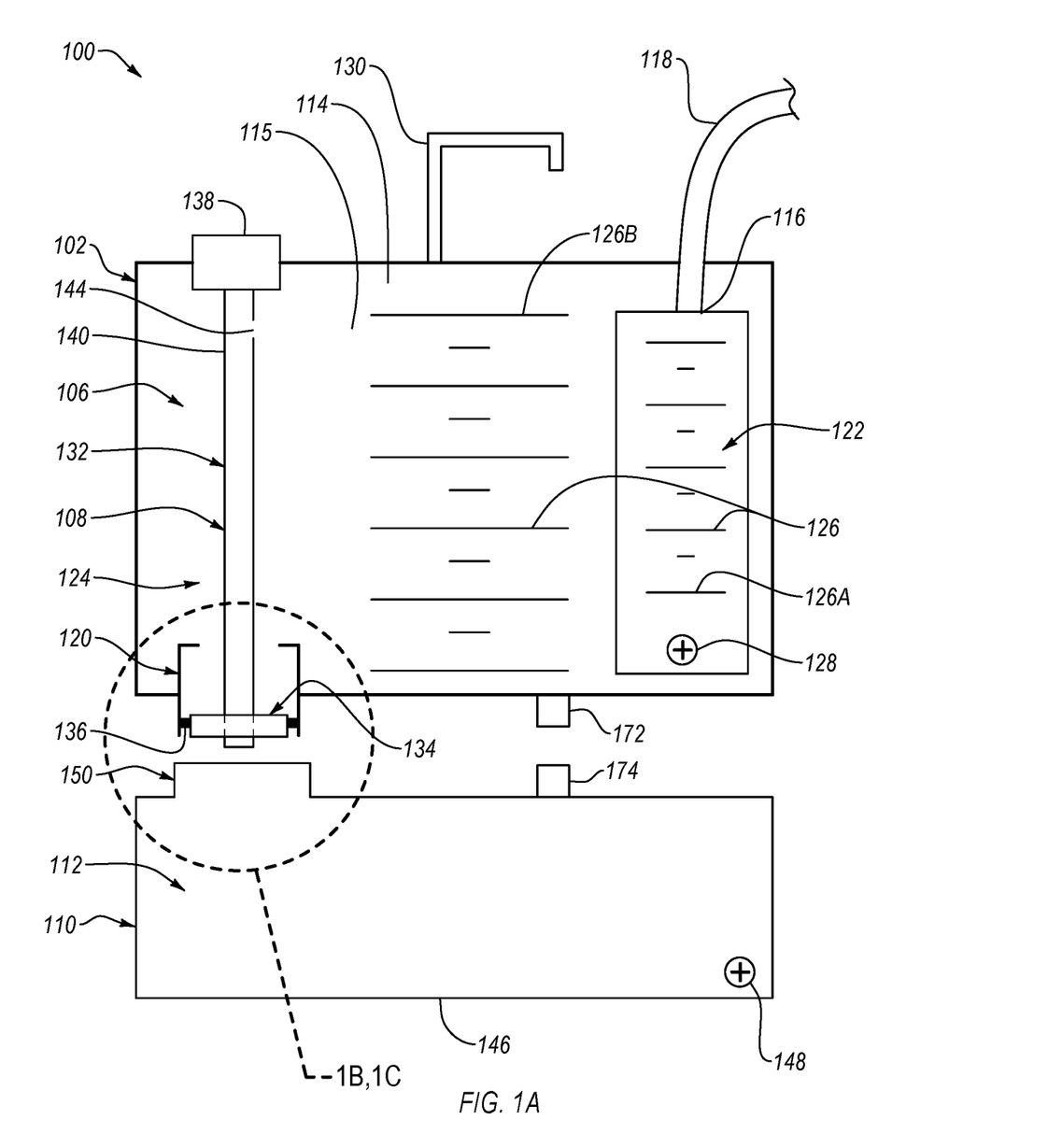
FIG. 1A is a schematic cutaway view of a drainage bag system, according to an embodiment.

FIG. 1A is a schematic cutaway view of a drainage bag system 100, according to an embodiment. The drainage bag system 100 includes a drainage container 102 that defines a first interior space 106 configured to receive and hold a fluid from a patient therein. The drainage bag system 100 further includes a fluid dispensing device 108 that is configured to regulate flow of the fluid from the first interior space 106 of the drainage container 102. For example, the fluid dispensing device 108 may substantially prevent the flow of the fluid from and out of the first interior space 106 when deactivated and permit the flow of the fluid from and out of the first interior space 106 when activated. The drainage container 102 may be fluidly coupled to and reversibly attached to (e.g., may be attached to and detached from) a bag 110. The bag 110 defines a second interior space 112 configured to receive and hold at least a portion of the fluid held in the first interior space 106 of the drainage container 102.

In some embodiments, the drainage container 102 may include a support structure configured to lend support thereto. For example, the drainage container 102 may include an at least semi-rigid container (e.g., rigid container), a bag, or other suitable support structure that is configured to increase rigidity and/or additional support for the drainage container 102. In an embodiment, the drainage container 102 itself may support the bag 110.

The drainage container 102 includes one or more first walls 114 that define the first interior space 106. The one or more first walls 114 may be formed from one or more materials that are flexible, rigid, semi-rigid, resilient, any suitable material, or combinations of materials. The first walls 114 of the drainage container 102 may be connected and/or bonded together in a manner that forms an at least substantially fluid tight first interior space 106. In an embodiment, the first walls 114 may include front panel 115 and a back panel (e.g., back wall 582 shown in FIG. 5). At least a portion of the front panel 115 may include and/or be formed from one or more materials that are transparent and/or translucent, thereby permitting a user of the drainage bag system 100 to determine a volume of fluid within the first interior space 106. The back panel may include and/or be formed from one or more materials that are transparent, translucent, and/or opaque. In an embodiment, the first walls 114 may include polyvinyl chloride ("PVC"), a di-2-ethylhexyl phthalate ("DEHP") free polymer (e.g., DEHP-free PVC), or any other suitable material.

The drainage container 102 may exhibit any suitable geometry. For example, the illustrated drainage container 102 exhibits a generally rectangular geometry. However, the drainage container 102 may exhibit a generally circular geometry, a generally heart-shaped geometry, a generally cylindrical geometry, or any other suitable geometry. In an embodiment, the drainage container 102 may exhibit a geometry that minimizes the height (e.g., vertical profile) of the drainage container 102. For example, the drainage container 102 may exhibit a geometry that maximizes the width (e.g., the width is equal to or greater than the height) of the drainage container 102 and/or the thickness (e.g., measured from the front wall 580 to the back wall 582 shown in FIG. 5). Such geometry may facilitate usage of the drainage bag system 100 in a space having a low vertical profile, such as under a low profile bed.

The drainage container 102 includes a first inlet 116 configured to accept a fluid from a patient into the first interior space 106. The first inlet 116 may be at least partially defined by the first walls 114 or may include a device coupled to the first wall 114. In an embodiment, the drainage container 102 may be used in a Foley catheter system. In such an embodiment, the first inlet 116 may receive or connect to a drainage tube 118 that is in fluid communication with a Foley catheter (not shown). In an embodiment, the first inlet 116 may include an anti-reflux valve (not shown). The drainage container 102 also includes a first outlet 120 formed at or near a bottom portion of the drainage container 102 or other suitable location.

The first interior space 106 may include one or more compartments (e.g., two or more compartments) formed therein. In an embodiment, the first interior space 106 may include a first compartment 122 and a second compartment 124. The first compartment 122 may be smaller than, substantially the same size as or larger than the second compartment 124. The first compartment 122 may be configured to receive and hold a fluid that enters the first interior space 106. For example, the first inlet 116 may be fluidly coupled to and dispense a fluid into the first compartment 122. The first compartment 122 may be fluidly coupled to the second compartment 124. For example, the first compartment 122 may be configured to contain a selected volume of the fluid therein and allow overflow of the fluid into the second compartment 124 when the drainage container 102 receives more than the selected volume of fluid. In other embodiments, the first interior space 106 may include a single compartment, or may include three or more compartments. In some embodiments, the first interior space 106 includes at least two compartments that are fluidly coupled to each other or isolated from each other.

In some embodiments, the drainage container 102 may include one or more graduated marking 126 that may indicate a volume of fluid collected therein. For example, the graduated markings 126 may facilitate determining the volume of fluid discharged by a patient during a time span. The graduated markings 126 may be formed on, for example, the first wall 114. In an embodiment, the first compartment 122 may include one or more first graduated markings 126A and the second compartment 124 may include one or more second graduated markings 126B. For example, the first graduated markings 126A may be used to determine the volume of the fluid that initially enters the first compartment 122 and the second graduated markings 126B may be used to determine the volume of fluid that is stored in the second compartment 124 after the first compartment 122 overflows.

In an embodiment, the drainage container 102 may include one or more first sampling ports 128 formed therein. The first sampling ports 128 may be configured to permit a user (e.g., a physician, a nurse, or medical technician) to take samples of a fluid stored in the drainage container 102 in an at least substantially sterile and fluid tight manner. For example, the first sampling port 128 may permit a user to take samples of the fluid using a syringe device, such as a catheter tip syringe or syringes with needles. In operation, a needle-like portion of the syringe device may be inserted though the first sampling port 128 into the first interior space 106. The first sampling port 128 may reseal itself in an at least substantially fluid tight manner after the user takes samples and removes the needle of the syringe device from the first sampling port 128. In some embodiments, the first sampling port 128 may be configured to permit the user to take multiple samples of the fluid from the drainage container 102. The first sampling port 128 may be positioned on any portion of the drainage container 102. For example, the illustrated first sampling port 128 is positioned to permit the user to sample a fluid present in the first compartment 122. In other embodiments, the first sampling port 128 may be positioned on the drainage container 102 to permit the user to sample a fluid from the second compartment 124, or another portion of the first interior space 106.

The drainage container 102 may include a hook 130 or other attachment mechanism configured to attach to an object (not shown). In other embodiments, the drainage container 102 may include Velcro, a string, an adhesive, or other suitable device configured to attach the drainage container 102 to an object. The object to which the drainage container 102 can be attached includes, for example, a bed frame, a wheel chair, or another object near or on a patient who is fluidly coupled to drainage container 102.

As discussed above, the fluid dispensing device 108 of the drainage bag system 100 is configured to regulate the flow of the fluid from the first interior space 106 through and out of the first outlet 120. For example, the fluid dispensing device 108 may substantially prevent the fluid from flowing through the first outlet 120 when deactivated. The fluid dispensing device 108 may also permit the fluid to flow through the first outlet 120 when activated. As such, the fluid dispensing device 108 may be in fluid communication with the first interior space 106 to regulate the flow of the fluid therefrom.

In the illustrated embodiment, the fluid dispensing device 108 includes a valve system 132. The valve system 132 includes a piston 134 configured to be reversibly displaced from a first position (e.g., deactivated) to a second position (e.g., activated). The piston 134 may be configured to substantially prevent the fluid present in the first interior space 106 from flowing through the first outlet 120 when the piston 134 is in the first position and permit the fluid to flow through and out of the first outlet 120 when the piston 134 is in the second position. For example, when the piston 134 is in the first position, the piston 134 may be at least partially positioned in the first outlet 120. The piston 134 may also exhibit a diameter (e.g., maximum diameter) and/or cross-sectional area that is substantially the same as or greater than the inner diameter and/or cross-sectional area of a portion of the first outlet 120 that is immediately adjacent the piston 134 when the piston 134 is in the first position. For example, the piston 134 may include a disk, cylinder, or other suitable shape that that tightly fits within the first outlet 120 when in the first position. As such, the piston 134 may substantially prevent the fluid in the first interior space 106 from flowing through and out of the first outlet 120 when the piston 134 is in the first position. The piston 134 may further include a seal 136 that further prevents the fluid from flowing around the piston 134 and through the first outlet 120. The seal 136 may include an O-ring that defines a diameter (e.g., maximum diameter) of the piston 134, a gasket, grease, or any other suitable seal. However, in other embodiments, the piston 134 itself may be formed of a compressible, resilient material (e.g., a rubber) so that the piston 134 also functions as the seal 136. Additionally, when the piston 134 is in the second position, the piston 134 may be at least partially (e.g., completely) positioned outside of the first outlet 120 (e.g., inside the first interior space 106 or outside of the drainage container 102) or positioned in a portion of the first outlet 120 that exhibits a diameter and/or cross-sectional area that is greater than the diameter and/or cross-sectional area of the piston 134. As such, when the piston 134 is in the second position, the fluid present in the first interior space 106 may freely flow through and out of the first outlet 120.

A manually-operable valve actuator 138 may be operably coupled to the piston 134. The manually-operable valve actuator 138 may be positioned and configured to be pushed, pulled, twisted, or otherwise manipulated by a user to reversibly move the piston 134 between the first and second positions. For example, at least one of the first walls 114 may define a hole therein configured to have the manually-operable valve actuator 138 at least partially positioned therein. The manually-operable valve actuator 138 and/or the hole may be configured to substantially prevent the fluid present in the drainage container 102 from leaking between the manually-operable valve actuator 138 and the hole, such as via a seal, a gasket, or other suitable mechanism that seals the manually-operable valve actuator 138 with the drainage container 102. The manually-operable valve actuator 138 may be configured to selectively move the piston 134 from the first position to the second position, or vice versa, when the manually-operable valve actuator 138 is manipulated by the user. In an embodiment, the manually-operable valve actuator 138 may be positioned at or near an uppermost portion of the drainage container 102. As such, a user of the drainage bag system 100 may not need to bend as much, if at all, to activate the fluid dispensing device 108.

In an embodiment, the manually-operable valve actuator 138 is directly attached to the piston 134. In an embodiment, the manually-operable valve actuator 138 may be spaced from the piston 134. In such an embodiment, the manually-operable valve actuator 138 may be operably coupled to the piston 134 via an elongated member 140, such as a shaft. For example, the elongated member 140 may extend from the manually-operable valve actuator 138 to the piston 134. For example, the piston 134 may define a hole that receives and is attach to the elongated member 140 (e.g., via interference fit), or the elongated member 140 may be attached to the piston 134 by other technique such as adhesive bonding or other suitable technique. In an embodiment, at least one of the first walls 114 may define a hole therein configured to have the elongated member 140 at least partially positioned in the hole. The manually-operable valve actuator 138 and/or the hole may be configured to substantially prevent the fluid present in the drainage container 102 from leaking between the elongated member 140 and the hole. In such an embodiment, the manually-operable valve actuator 138 may be positioned above the uppermost portion of the drainage container 102.

In some embodiments, the manually-operable valve actuator 138 may be manipulated (e.g., pressed or pulled) to move the piston 134 from the first position to the second position. Similarly, the manually-operable valve actuator 138 may be manipulated (e.g., the other of pressed or pulled) to move the piston 134 from the second position to the first position. In an embodiment, the valve system 132 may include a biasing element (e.g., a spring or other resilient, compressible member such as a rubber material) that is configured to bias and return the piston 134 from the second position to the first position without the manually-operable valve actuator 138 being manipulated.

It should be noted that, in other embodiments, the actuator 138 may be computer-controlled by a computer system, such as a desktop computer, laptop computer, a tablet, or the like. Such a computer may automatically actuate the actuator 138 after a selected period of time or after the first compartment 122 and/or the second compartment 124 is filled with a selected volume of fluid. For example, the actuator 138 may be hydraulically actuated, pneumatically actuated, magnetically actuated, or actuated by another suitable technique by the computer.

In some embodiments, the fluid dispensing device 108 may be configured to permit the flow of the fluid from the first interior space 106 through and out of the first outlet 120 when a volume of the fluid present in the first interior space 106 exceeds a selected volume. For example, in the illustrated elongated member 140 is at least partially hollow that includes an elongated member inlet 144 that fluidly couples the first interior space 106 to the hollow portion of the elongated member 140. The hollow portion of the elongated member 140 may extend from the elongated member inlet 144 to a portion of the first outlet 120 that is not in fluid communication with the piston 134 (e.g., the hollow portion may extend through the piston 134). As such, when the level of the fluid in the drainage container 102 reaches the elongated member inlet 144, the fluid may overflow into the hollow portion of the elongated member 140 and out of the first outlet 120 into the second interior space 112 of the bag 110. In an embodiment, the piston 134 may be configured to move from the first position to the second position when the volume of the fluid present in the first interior space 106 exceeds the certain volume. For example, when the volume of the fluid present in the first interior space 106 exceeds the certain volume, the weight of the fluid present in the first interior space 106 may exert a force on the piston 134 that is greater than a biasing device (not shown) operably coupled to the piston 134 may support. For example, the biasing device may include a spring, a resilient element made of a polymeric material, or combinations thereof. As such, the weight of the fluid may cause the piston 134 to move from the first position to the second position.

In other embodiments, the fluid dispensing device 108 may include other suitable devices. For example, the fluid dispensing device 108 may include any device that may be deactivated (e.g., substantially prevent the flow of a fluid through the first outlet 120) and activated (e.g., permit the flow of the fluid through the first outlet 120). For example, the fluid dispensing device 108 may include a valve (e.g., ball valve, slide valve, etc.) that is configured to substantially prevent the flow of a fluid through the first outlet 120 when deactivated and permit the flow of the fluid through the first outlet 120 when activated (e.g., turning a knob, lever, handle, etc.). In an embodiment, the fluid dispensing device 108 may include a device configured to be activated (e.g., at least partially activated) when the fluid in the first interior space 106 reaches or exceeds a certain amount.

As previously discussed, the drainage container 102 may include a plurality of compartments, such as the first compartment 122 and the second compartment 124. In some embodiments, the first compartment 122 may be configured to drain a fluid therein into the second compartment 124 (e.g., when the fluid dispensing device 108 is activated) thereby emptying at least a portion of the fluid from the first compartment 122. For example, the fluid dispensing device 108 may be configured to form a portion of a barrier between the first compartment 122 and the second compartment 124. When the fluid dispensing device 108 is deactivated, the fluid dispensing device 108 may prevent the flow of the fluid from the first compartment 122 into the second compartment 124. However, when the fluid dispensing device 108 is activated, the fluid dispensing device 108 may permit the flow of the fluid into the second compartment 124 and/or the second interior space 112. For example, the piston 134 may form a portion of the barrier when the piston 134 is in the first position and may open the barrier when the piston 134 is in the second position. In another embodiment, the drainage container 102 may include a second fluid dispensing device (not shown). The second fluid dispensing device may be configured to substantially prevent the fluid from the first compartment 122 from flowing into the second compartment 124 when deactivated and may permit the flow of at least a portion of the fluid within the first compartment 122 flow into the second compartment 124 when activated. For example, the second fluid dispensing device may be substantially similar to the valve system 134.

As discussed above, the bag 110 of the drainage bag system 100 is configured to collect fluid from the drainage container 102. The bag 110 defines the second interior space 112, which is configured to receive and store at least a portion of the fluid stored in the first interior space 106. Similar to the drainage container 102, the bag 110 may include any device that defines the second interior space 112. In an embodiment, the bag 110 may include one or more second walls 146 that define the second interior space 112. The one or more second walls 146 may include and/or be formed from a flexible, semi-rigid, rigid, resilient, or any suitable material or combinations of materials. In any event, the second walls 146 may be connected and/or bonded together in a manner that forms or defines an at least substantially fluid tight second interior space 112. In some embodiments, at least a portion of the one or more second walls 146 may be transparent and/or translucent. The transparent and/or translucent second wall 146 may permit a user to visual inspect the bag 110 to determine the volume of a fluid present in the second interior space 112 (e.g., using graduated markings). In an embodiment, the second walls 146 may include PVC, a DEHP-free polymer, or any other suitable material. In an embodiment, the bag 110 may be less rigid than the drainage container 102. In an embodiment, the bag 110 may hold a lesser volume, substantially equal volume, or greater volume of fluid than the drainage container 102.

The bag 110 may exhibit any suitable geometry. For example, the one or more second walls 146 may form three dimensional shapes, such as a generally cylindrical shape, a generally spherical shape, a generally box-like shape, or another suitable shape. In another example, the bag 110 may exhibit a geometry that is substantially similar to the drainage container 102 or a geometry that is substantially different from the drainage container 102. In an embodiment, the bag 110 may exhibit a geometry that substantially corresponds to the geometry of the drainage container 102. For example, if a portion of the drainage container 102 most proximate to the bag 110 exhibits a convex shape, the bag 110 may exhibit a concave shape that partially encloses the convex shape of the drainage container 102. In an embodiment, the bag 110 may exhibit a geometry that minimizes the height (e.g., vertical profile) of the bag 110. For example, the bag 110 may exhibit a geometry that maximizes the width (e.g., the width is equal to or greater than the height) and/or the thickness of the bag 110. Such geometry may facilitate usage of the drainage bag system 100 in a space having a low vertical profile, such as under a low profile bed.

Similar to the drainage container 102, the bag 110 may include one or more second sampling ports 148 formed in the one or more second walls 146. The second sampling ports 148 may be configured to permit a user to take samples of a fluid that is present in the second interior space 112. For example, the second sampling port 148 may permit a user to take a sample of the fluid using a syringe device. The second sampling ports 148 may form an at least substantially fluid tight seal when a user is not taking a sample of the fluid through the second sampling ports 148. The second sampling ports 148 may be configured to permit the user to take multiple samples therefrom without disrupting the fluid tight seal.

The bag 110 may include one or more second inlets 150 formed in the one or more second walls 146. The second inlet 150 may be configured to reversibly attach to the first outlet 120 in an at least substantially fluid tight manner. In some embodiments, the second inlet 150 may form an at least substantially fluid tight seal when the first outlet 120 is not attached to the second inlet 150. In other embodiments, the second inlet 150 may be configured to be sealed in an at least substantially fluid tight manner by placing a cap over an opening thereof or using another suitable device that substantially prevents a fluid from exiting the second interior space 112.

Figures 1B, 1C:
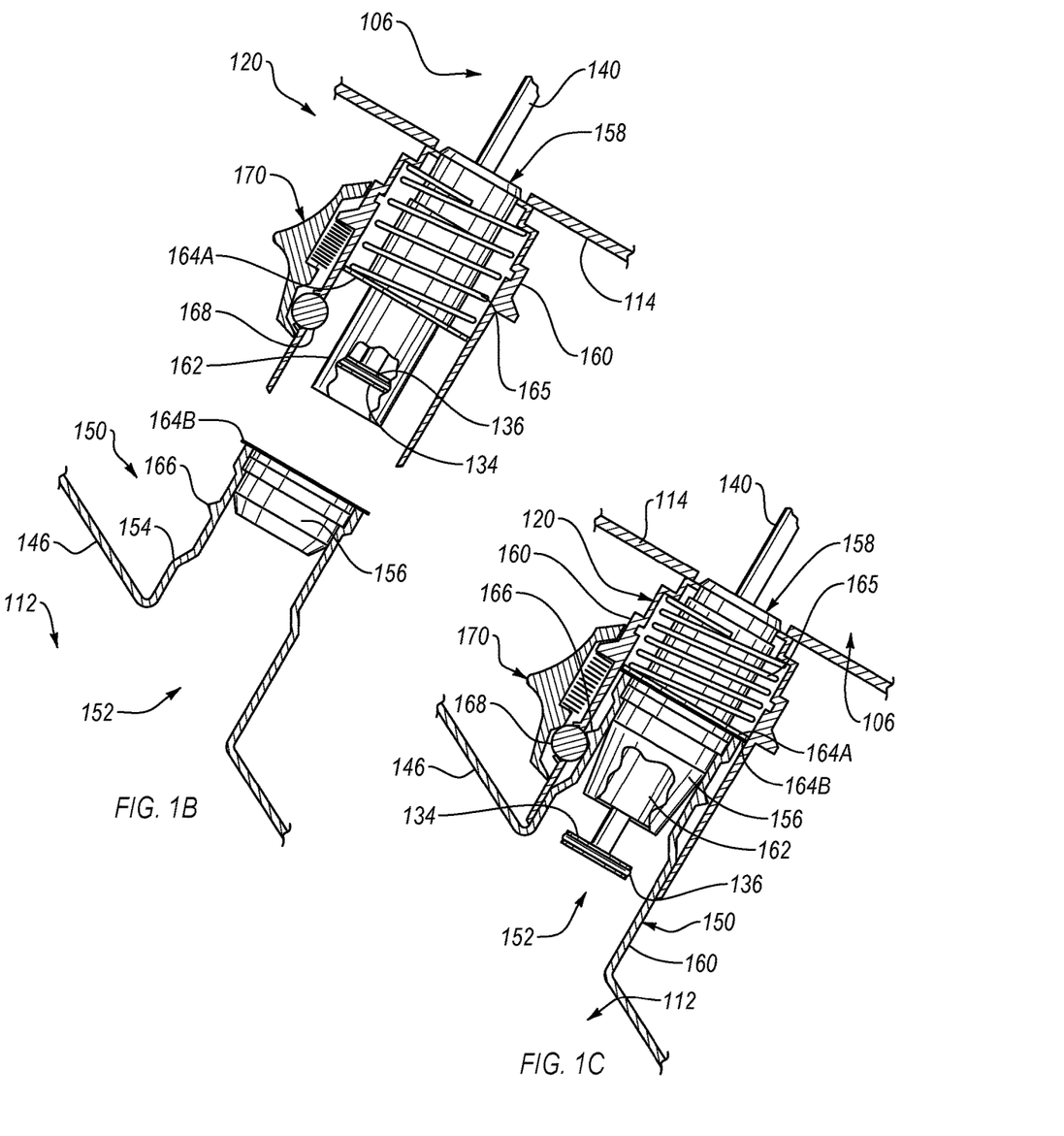
FIG. 1B is a partial, cutaway, enlarged view of the first outlet and the second inlet of the drainage bag system taken from the region 1B, 1C shown in FIG. 1A, according to an embodiment.
FIG. 1C is a partial, cutaway, enlarged view of the first outlet shown in FIG. 1B reversibly fluidly coupled to the second inlet shown in FIG. 1B, according to an embodiment.

FIGS. 1B and 1C provide more details about one or more embodiments for fluidly coupling the drainage container 102 and the bag 110 together, and the operation of the fluid dispensing device 108. FIG. 1B is a partial, cutaway, enlarged view of the first outlet 120 and the second inlet 150 of the drainage bag system 100 taken from the region 1B, 1C shown in FIG. 1A, according to an embodiment. FIG. 1C is a partial, cutaway, enlarged view of the first outlet 120 shown in FIG. 1B reversibly coupled to the second inlet 150 shown in FIG. 1C in an at least substantially fluid tight manner, according to an embodiment.

Referring to FIG. 1B, in the illustrated embodiment, the second inlet 150 of the bag 110 includes a second opening 152 that is defined by the second wall 146. The second opening 152 may be of sufficient size to permit the fluid to flow therethrough. For example, the second opening 152 may be of sufficient size to permit the fluid to flow therethrough without the application of external pressure. The second inlet 150 also includes at least one inlet wall 154 coupled to a portion of the second wall 146 that defines the second opening 152 and extends away from the second interior space 112.

The second inlet 150 also includes a sealing device 156 that fluidly seals the second interior space 112 when the first outlet 120 is not reversibly coupled to (e.g., detached from) the second inlet 150. The sealing device 156 may be bonded or otherwise attached to the inlet wall 154 and form an at least substantially fluid tight seal when the first outlet 120 is not fluidly coupled to the second inlet 150 (FIG. 1B). For example, the illustrated sealing device 156 may define through hole (e.g., an annular seal) that is initially closed in an at least substantially fluid tight manner. When the first outlet 120 is fluidly coupled to the second inlet 150 (FIG. 1C), the illustrated sealing device 156 may stretch, conform to the first outlet 120, or otherwise open the through hole. As such, the sealing device 156 may form an at least substantially fluid tight seal when the first outlet 120 is fluidly coupled to the second inlet 150. The illustrated sealing device 156 may reseal itself in an at least substantially fluid tight manner after the user de-couples the first outlet 120 from the second inlet 150 (FIG. 1B). As such, the sealing device 156 may provide a substantially closed system, thereby substantially preventing contamination of an exterior of the drainage bag system 100 or an area about the drainage bag system 100. In an embodiment, the sealing device 156 may also maintain a fluid tight and/or wipe at least some of the fluid from an exterior the first outlet 120 of the drainage container 102 as the first outlet 120 is de-coupled from the second inlet 150. In other embodiments, the sealing device 156 may include a plurality of flaps that form an at least substantially fluid tight seal in their relaxed state, a cap or lid, a clamp, or any other suitable sealing device.

Referring still to FIG. 1B, in the illustrated embodiment, the first outlet 120 includes a first opening 158 that is defined by the first wall 114 of the drainage container 102. The first opening 158 may be of sufficient size to permit the fluid to flow therethrough. For example, the first opening 158 may be of sufficient size to permit the fluid to flow therethrough without the application of external pressure (e.g., compressing the drainage container 102). The first outlet 120 may also include an outlet wall 160 coupled to the portion of the first wall 114 that defines the first opening 158 and extends away from the first interior space 106. The outlet wall 160 may exhibit a size and shape configured to encircle at least a portion of the inlet wall 154, or vice versa.

In the illustrated embodiment, the first outlet 120 may include a hollow structure 162 (e.g., a tube) that is positioned within the outlet wall 160. As such, the hollow structure 162 may exhibit an exterior diameter that is less that the interior diameter of the outlet wall 160. For example, the hollow structure 162 may include a hollow generally cylindrical tube or another suitable hollow structure.

In an embodiment, the first outlet 120 may include a first barrier 164a that extends between the outlet wall 160 and the hollow structure 162. The first barrier 164a may form an at least substantially fluid tight seal between the outlet wall 160 and the hollow structure 162 such that the fluid from first interior space 106 cannot flow past or through the first barrier 164a. Similarly, the second inlet 150 may include a second barrier 164b that is configured to press against the first barrier 164a when the first outlet 120 is fluidly coupled to the second inlet 150. For example, the first barrier 164a may include a flexible seal or gasket, or rigid structure.

Referring to FIG. 1C, in an embodiment, the first barrier 164a may be configured to move towards the first wall 114 when the second barrier 164b is pressed against the first barrier 164a. In such an embodiment, the first outlet 150 may include a spring 165 or other compressible, resilient element that pushes the first barrier 164a against the second barrier 164b when first outlet 120 is fluidly coupled to the second inlet 150. Similarly, the spring 165 may move the first barrier 164a away from the first wall 114 when the first outlet 120 is fluidly detached from the second inlet 150 such that the first barrier 164a is in its original position as shown in FIG. 1B. In an embodiment, at least one of the first barrier 164a or the second barrier 162b may be omitted. For example, the hollow structure 162 may be directly bonded to the outlet wall 160 and/or first wall 114 such that a fluid cannot flow between the outlet wall 160 and the hollow structure 162.

The hollow structure 162 may include at least a portion of the fluid dispensing device 108 positioned therein. For example, the piston 134 may be positioned within the hollow structure 162 when the piston 134 is in the first position (FIG. 1B). The piston 134 may exhibit a size and/or shape that substantially conforms with the inner diameter and/or shape of the hollow structure 162. As such, the seal 136 of the piston 134 may form a substantially fluid tight seal with the hollow structure 162 when in the first position. Additionally, at least a portion of the elongated member 140 coupled to the piston 134 may also be positioned within the hollow structure 162.

Referring still to FIG. 1C, when the manually-operable valve actuator 138 is actuated, the piston 134 may move from the first position into the second position. When the piston 134 is in the second position, the piston 134 may be positioned outside the hollow structure 162 or may be positioned adjacent to a portion of the hollow structure 162 that exhibits a greater inner cross-sectional area (e.g., greater inner diameter) than the portion of the hollow structure 162 adjacent to the piston 134 when the piston 134 is in the first position. When the piston 134 is in the second position, the fluid in the first interior space 106 may freely flow through the hollow structure 162 and around the piston 134 into the second interior space 112 of the bag 110.

In some embodiments, the hollow structure 162 may be configured to change the sealing device 156 from its relaxed state to its activated state. For example, the hollow structure 162 may be formed of a rigid or semi-rigid material that is configured to press against and through the sealing device 156. Referring to FIG. 1C, in the illustrated embodiment, the hollow structure 162 is pressed against the sealing device 156 and stretches or otherwise opens the sealing device 156.

In operation, the user physically and fluidly couples the first outlet 120 of the drainage container 102 to the second inlet 150 so that the hollow structure 162 presses against the sealing device 156 to thereby stretch or otherwise open the sealing device 156 so that fluid can flow through the sealing device 156 into the bag 110. However, the fluid from the first interior space 106 may not flow therefrom into the second interior space 112 when the piston 134 is in the first position. However, as illustrated in FIG. 1C, the piston 134 may be moved from the first position to the second position (e.g., in the second interior space 112) when the manually-operable valve actuator 138 is actuated.

The first outlet 120 and the second inlet 150 may be configured to be reversibly coupled to each other such that the first outlet 120 and the second inlet 150 are not inadvertently disconnected. In the illustrated embodiment, the inlet wall 154 may include an obstruction 166, such as a ridge, recess, or other suitable obstruction. The outlet wall 160 may include a node 168 that extends at least from an inner surface of the outlet wall 160. In some embodiments, the node 168 may be configured to move relative to the outlet wall 160 (e.g., retract). In such embodiments, the first outlet 120 may include a locking/releasing device 170 that selectively permits or restricts movement of the node 168. The node 168 may be configured to slip over the obstruction 166 when the first outlet 120 and the second inlet 150 are mated together. The node 168 and the obstruction 166 may be configured to prevent the node 168 from slipping back over the obstruction 166 unless a certain force is applied and/or the locking/releasing device permits the node 168 to retract away from the outlet wall 160. In other embodiments, the first outlet 120 and the second inlet 150 may be reversibly attached to each other using a threaded connection, a pin, or other known securing mechanisms.

In an embodiment, at least one of the first outlet 120 or the second inlet 150 may include a check valve that permits the fluid to flow from the first interior space 106 into the second interior space 112, but substantially prevents the fluid from flowing from the second interior space 112 into the first interior space 106. In an embodiment, the valve system 132, and in particular the piston 134, may act as the check valve. In other embodiments, at least one of the first outlet 120 or the second inlet 150 may include a device that is separate from the valve system 132 that acts as the check valve.

FIGS. 1B and 1C merely illustrate an embodiment of the fluid dispensing device 108, the first outlet 120, and the second inlet 150. However, the fluid dispensing device 108, the first outlet 120, and the second inlet 150 may exhibit different configurations. For example, U.S. Pat. No. 8,777,912 discloses examples of a drainage bag that is secured to another object in an at least substantially fluid tight manner that may be used to practice any of the embodiments disclosed herein. U.S. Pat. No. 8,777,912 is incorporated herein, in its entirety, by this reference.

Referring again to FIG. 1A, in some embodiments, the drainage container 102 (e.g., the drainage container 102) and the bag 110 may be reversibly coupled together at one or more additional locations that are spaced from the first outlet 120 and the second inlet 150. In an embodiment, the drainage container 102 may include a first attachment device 172 and the bag 110 may include a second attachment device 174. The first attachment device 172 is configured to reversibly attach to the second attachment device 174. For example, the first attachment device 172 may include a loop and the second attachment device 174 may include a hook, or vice versa. In another example, the first attachment device 172 and the second attachment device 174 may both include a respective hook. In an embodiment, at least one of the first attachment device 172 or the second attachment device 174 may include a magnet and the other of the first attachment device 172 or the second attachment device 174 may include a magnetically attractable object, such as oppositely poled magnet or a ferromagnetic material. In other embodiments, only one of the drainage container 102 or the bag 110 may include an attachment mechanism. For example, one of the drainage container 102 or the bag 110 may include a clamp that is configured to reversibly attach to the other of the drainage container 102 or the bag 110.

In an embodiment, any portion of the drainage bag system 100 that is exposed to the fluid may include a coating thereon configured to substantially prevent microbes from growing thereon. For example, at least one of the first interior space 106, the second interior space 112, the fluid dispensing device 108, the first outlet 120, the second inlet 150, or another component of the drainage bag system 100 may include the coating applied to at least a portion of a surface thereof that is exposed to the fluid. The coating may include a hydrophobic coating or any suitable antimicrobial coating.

Figure 2:
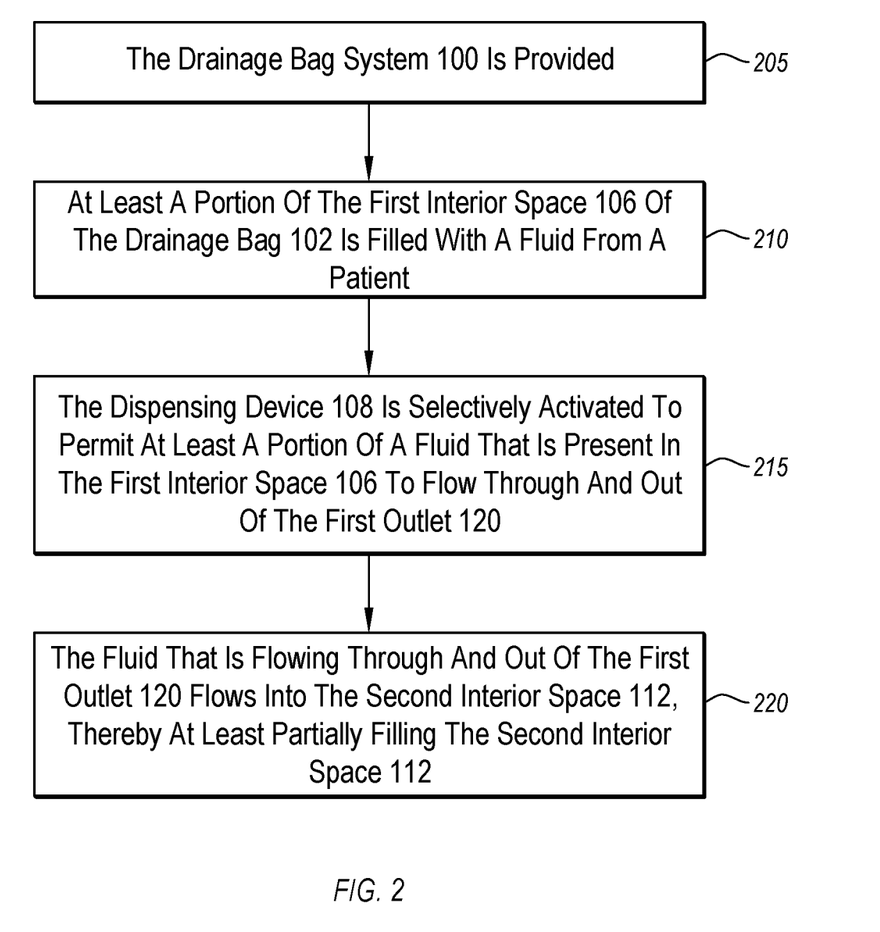
FIG. 2 is a flow diagram of a method of using the drainage bag system shown in FIGS. 1A-1C, according to an embodiment.

FIG. 2 is a flow diagram of a method 200 of using the drainage bag system 100 shown in FIGS. 1A to 1C, according to an embodiment. The acts of the method 200 may be performed in any order. In some embodiments, some of the acts of the method 200 may be split into a plurality of acts, some of the acts may be combined into a single act, and some acts may be omitted. Also, it is understood that additional acts can be added to the method 200.

In act 205, the drainage bag system 100 is provided, which as previously discussed, includes the drainage container 102, the fluid dispensing device 108, and the bag 110. In act 210, at least a portion of the first interior space 106 is filled with a fluid from a patient. For example, the drainage container 102 may be fluidly coupled to a patient (e.g., using a urinary drainage system that includes the drainage tube 118 coupled to a urinary catheter) and a fluid (e.g., urine) from the patient may flow into the first interior space 106. In an embodiment, the drainage container 102 includes the first compartment 122 and the second compartment 124. In such an embodiment, the fluid from the patient may initially fill the first compartment 122. A portion of the fluid that fills the first compartment 122 may fill the second compartment 124, for example, after the first compartment 122 is filled above a certain level.

In act 215, the fluid dispensing device 108 may be selectively activated to permit at least a portion of a fluid that is present in the first interior space 106 to flow through and out of the first outlet 120. The fluid dispensing device 108 may be selectively activated by a user by manipulating the fluid dispensing device 108. For example, the manually-operable valve actuator 138 of valve system 132 may be manipulated by the user. Manipulating the manually-operable valve actuator 138 may cause the piston 134 to move from the first position (e.g., deactivated) to the second position (e.g., activated).

In act 220, the fluid that is flowing through and out of the first outlet 120 may flow into the second interior space 112, thereby at least partially filling the second interior space 112. For example, the fluid may flow through the first outlet 120 and into the second interior space 112 in an at least substantially fluid tight manner.

In an additional act, the fluid dispensing device 108 may be selectively deactivated to substantially prevent the fluid from flowing from the first interior space 106 and through the first outlet 120. For example, the fluid dispensing device 108 may be selectively deactivated after substantially all of the fluid present in the first interior space 106 has flowed therefrom, after a substantial portion (e.g., substantially all of) the second interior space 112 is filled with the fluid, or after some fluid has flowed through the first outlet 120. In an embodiment, the fluid dispensing device 108 may be deactivated (e.g., move the piston 134 from the second position to the first position) by manipulating the manually-operable valve actuator 138. Alternatively, the fluid dispensing device 108 may be deactivated by ceasing to manipulate the manually-operable valve actuator 138. For example, the valve system 132 may include a biasing device that moves the piston 134 from the second position back to the first position.

In an embodiment, the user may detach the bag 110 from the drainage container 102. For example, the user may decouple the first outlet 120 from the second inlet 150. The first outlet 120 and/or the second inlet 150 may automatically form an at least substantially fluid tight seal when they are decoupled to prevent a fluid leaving the first interior space 106 and/or the second interior space 112, respectively. For example, the fluid dispensing device 108 (e.g., piston 134) may substantially seal the first outlet 120 when deactivated and the second inlet 150 may include a sealing device 156 that automatically seals the second inlet 150. In an embodiment, the first outlet 120 and/or the second inlet 150 may not automatically form an at least substantially fluid tight seal and may require an additional device (e.g., a lid) to be coupled thereto to form an at least substantially fluid tight seal. Additionally, the user may decouple the bag 110 from the drainage container 102 by detaching any additional attachment devices (e.g., the first attachment device 172 and the second attachment device 174).

In an embodiment, after the user detaches the bag 110 from the drainage container 102, the user may dispose at least a portion of the fluid that is held within the bag 110. In an embodiment, the user may dispose of the bag 110 by placing the bag 110 in the garbage, incinerating the bag 110, or may otherwise dispose of the bag 110. As such, the bag 110 may be formed of a material is biodegradable, does not release toxic fumes when burned, or any other disposable material. In an embodiment, the fluid held within the bag 110 may be removed from the second interior space 112. For example, the fluid may be removed from the second interior space 112 using the second sampling ports 148. In particular, a user may use a syringe-like device to remove at least some of the fluid from the second interior space 112 using the second sampling ports 148. In an embodiment, the bag 110 may include an outlet device (e.g., Bard® Safety-Flow™ outlet device). The outlet device (not shown) may be used to empty at least a portion of the fluid held within the bag 110 into another container. In an embodiment, the user may take samples from the bag 110 (e.g., using the second sampling port 148) prior to disposing the bag 110.

In an embodiment, after the user detaches the bag 110 from the drainage container 102, the user may attach a new bag (not shown) to the drainage container 102. The new bag may be configured to receive and hold at least a portion of a fluid that is held within the first interior space 106. For example, the new bag may define a new second interior space. In an embodiment, the new bag may be substantially similar to the bag 110. In an embodiment, the new bag may be substantially different from the bag 110. For example, the new bag may exhibit a different shape or size than the bag 110, the new bag may include different components than the bag 110, etc. The new bag may be attached to the drainage container 102 by fluidly coupling the first outlet 120 to a new second inlet of the new bag. Additionally, the new bag may be attached to the drainage container 102 using an attachment device that is spaced from the new second inlet.

The drainage bag system 100 may facilitate disposal of a fluid received from a patient. For example, the drainage container 102 may continuously receive a fluid from the patient even when a user is disposing of the fluid held within the first interior space 106 (e.g., flowing the fluid into the bag 110 and/or detaching the bag 110 from the drainage container 102). As such, there is no need to stop the flow of the fluid from the patient when disposing of the fluid. Additionally, in some embodiments, the drainage bag system 100 does not include a conventional collection bag outlet device that drains the fluid into a container that is distinct from the drainage bag system 100 (e.g., fluid container). As such, the drainage bag system 100 eliminates splashing that may occur when using conventional collection bag outlet devices.

Figure 3:
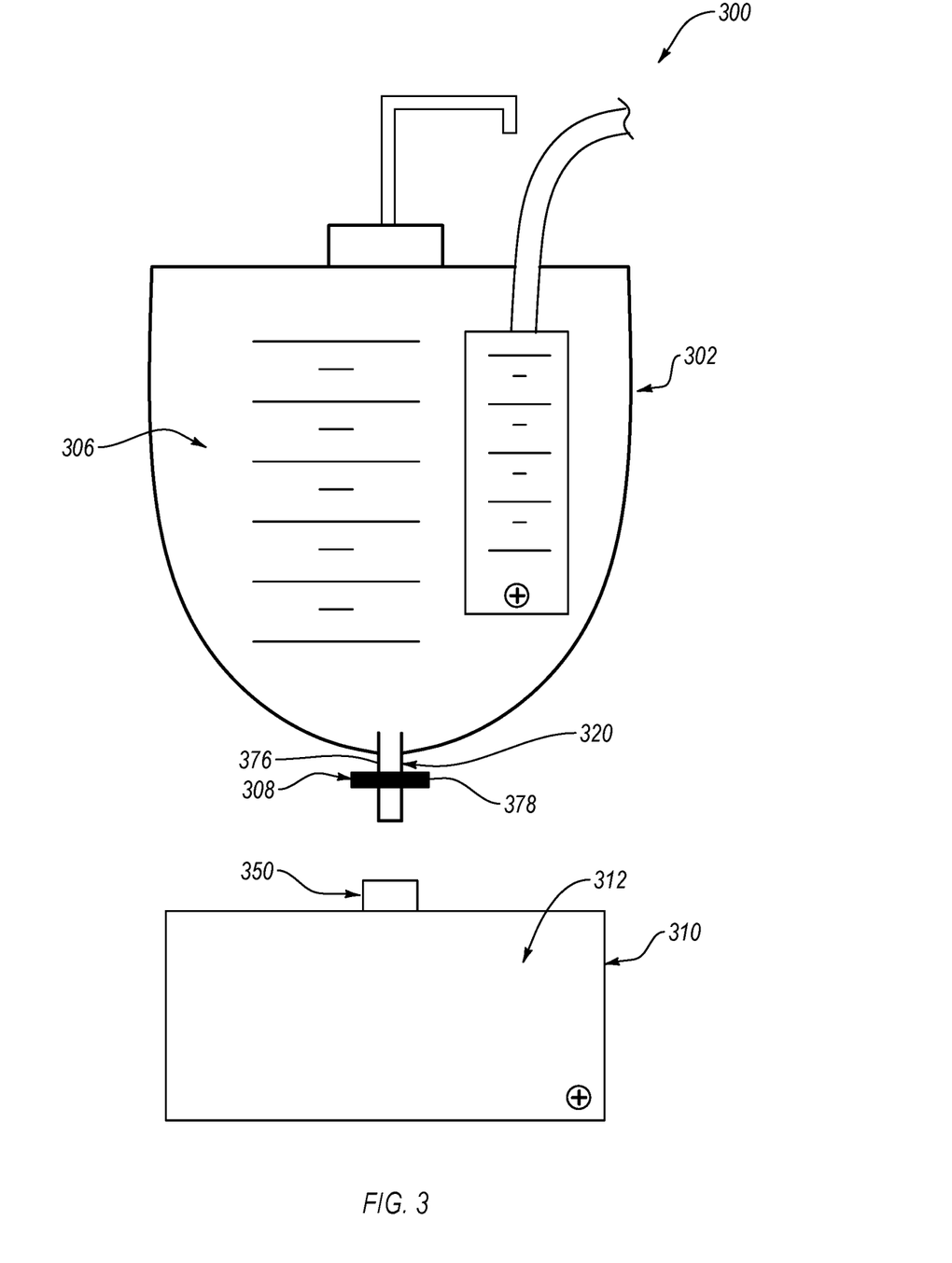
FIG. 3 is a schematic cutaway view of a drainage bag system, according to an embodiment.

FIG. 3 is a schematic cutaway view of a drainage bag system 300, according to an embodiment. Features illustrated in and described in relation to FIG. 3 may be used in any of the embodiments disclosed herein. The drainage bag system 300 is structurally similar to the drainage bag system 100 shown in FIG. 1. Therefore, in the interest of brevity, an explanation of the components in both drainage bag systems 100, 300 that are identical or similar to each other will not be repeated unless the components function differently in the drainage bag systems 100, 300.

The drainage bag system 300 may include a drainage container 302 that exhibits a generally heart-shaped geometry. The drainage bag container 302 may be formed from the same materials as the drainage container 102 and include one or more graduated markings thereon (not labeled). The drainage container 302 also defines a first interior space 306 configured to receive and hold a fluid therein. For example, the first interior space 306 may include a single compartment or may be divided into multiple compartments with corresponding graduated markings similar to the first interior space 106 of the drainage bag system 100 shown in FIG. 1A. The drainage container 302 further includes a first outlet 320. The drainage container 302 also include a fluid dispensing device 308 that is configured to regulate the flow of the fluid present in the first interior space 306 through the first outlet 320. For example, the fluid dispensing device 308 may be configured the same or similarly to the fluid dispensing device 108 and may substantially prevent the flow of the fluid from the first interior space 306 through the first outlet 320 when deactivated and may permit the flow of the fluid from the first interior space 306 through the first outlet 320 when activated. The drainage container 302 may be fluidly coupled and reversibly attached to a bag 310, which may be formed from the same materials as the bag 110. The bag 310 defines a second interior space 312 configured to receive and hold at least a portion of the fluid held in the first interior space 306. For example, the bag 310 may include a second inlet 350 that is fluidly coupled and reversibly attached to the first outlet 320.

In the illustrated embodiment, the first outlet 320 may include a conduit 376 that extends from the drainage container 302. In some embodiments, the conduit 376 may be configured to reversibly attach to a second inlet 350 of the bag 310. In other embodiments, the first outlet 320 may include another component (e.g., a component substantially similar to the first outlet 120 shown in FIGS. 1B and 1C) that is attached to the conduit 376 that is configured to reversibly attach to the second inlet 350. In other embodiments, the conduit 376 may be configured to be threadly coupled to the second inlet 350 via internal or external threads.

In an embodiment, at least a portion of the conduit 376 may include and/or be formed of a material that is flexible. The fluid dispensing device 308 may be configured to collapse the conduit 376 on itself when deactivated, thereby substantially preventing a fluid from flowing through the conduit 376. For example, the fluid dispensing device 308 may include a clamp 378, such as a catheter clamp. When the clamp 378 is tightened about and on the conduit 376 (e.g., deactivated), the conduit 376 may substantially prevent the fluid from flowing through the conduit 376. However, the clamp 378 may be activated by loosening (e.g., releasing) the clamp 378 about the conduit 376, thereby permitting the fluid to flow through and out of the first outlet 320. The conduit 376 may exhibit any length that is sufficient to have the clamp 378 or another fluid dispensing device 308 collapse the conduit 376 on itself.

Figure 4:
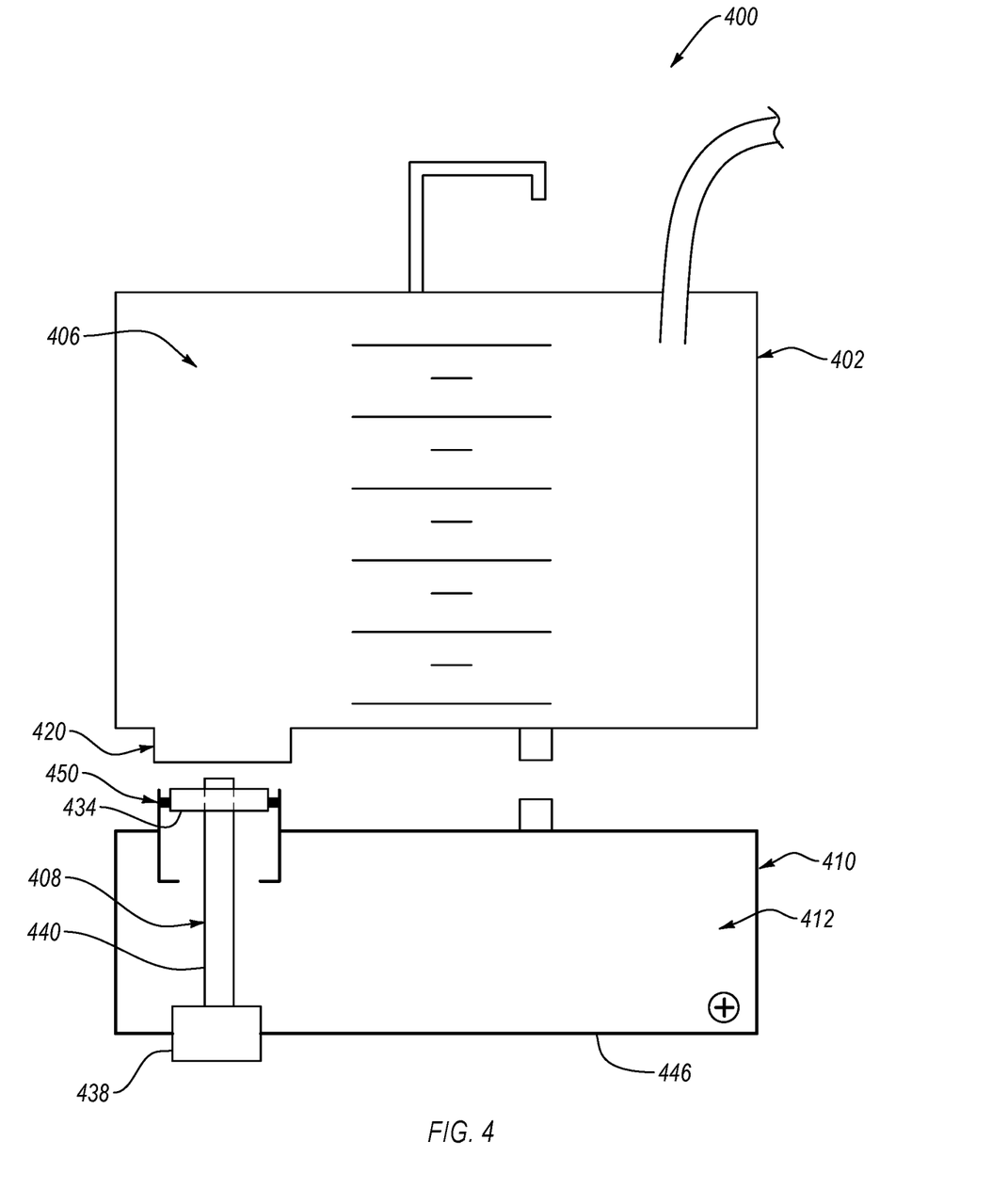
FIG. 4 is a schematic cutaway view of a drainage bag system, according to an embodiment.

FIG. 4 is a schematic cutaway view of a drainage bag system 400, according to an embodiment. The drainage bag system 400 is structurally similar to the drainage bag systems 100, 300 shown in FIGS. 1 and 3. Therefore, in the interest of brevity, an explanation of the components in both drainage bag systems 100, 300, 400 that are identical or similar to each other will not be repeated unless the components function differently in the drainage bag systems 100, 300, 400.

The drainage bag system 400 includes a drainage container 402 that defines a first interior space 406. The drainage bag container 402 may be formed from the same materials as the drainage container 102 and include one or more graduated markings thereon (not labeled). The first interior space 406 may include a single compartment that is configured to receive and hold a fluid from a patient therein. The drainage container 402 may include a first outlet 420. The drainage container 402 is fluidly coupled to a bag 410 that defines a second interior space 412. The bag 410 may be formed from the same materials as the bag 110. The second interior space 412 is configured to receive and hold at least a portion of the fluid held in the first interior space 406. The bag 410 includes second inlet 450 that is coupled to the first outlet 420.

The drainage bag system 400 further includes a fluid dispensing device 408 that is substantially similar to or the same as any of the fluid dispensing devices disclosed herein (e.g., the valve system 132, the clamp 378, or any other suitable fluid dispensing device). However, the fluid dispensing device 408 is in fluid communication with the bag 410. In an embodiment, the illustrated fluid dispensing device 408 is substantially similar to the fluid dispensing device 108 having the valve system 132 shown in FIGS. 1A-1C except that the fluid dispensing device 408 is at least partially positioned in the second interior space 412 of the bag 410. For example, the fluid dispensing device 408 may include a piston 434 that is configured to be moved from the first position (e.g., deactivated) to a second position (e.g., activated). As such, the piston 434 may exhibit a diameter and/or cross-sectional area that is substantially the same as an inner diameter and/or cross-sectional area of a portion of the second inlet 450 that is immediately adjacent the piston 434 when the piston 434 is in the first position. The fluid dispensing device 408 may also include a manually-operable valve actuator 438 that is operably coupled to the piston 434 (e.g., using an elongated member 440). The manually-operable valve actuator 438 may move the piston 434 from the first position to the second position, or vice versa, when the manually-operable valve actuator 438 is manipulated by a user. In an embodiment, the bag 410 may be formed from one or more second walls 446. In such an embodiment, at least one of the second walls 446 may define a hole that is configured to have the manually-operable valve actuator 438 at least partially positioned therein.

In an embodiment, the fluid dispensing device 408 may include a fluid dispensing device other than the valve system. For example, the fluid dispensing device 408 may include a clamp (not shown). In such an example, the bag 410 may include a conduit (not shown) that extends from the bag 410. The conduit may be configured to collapse on itself when a clamp tightens thereabout (e.g., deactivated) and substantially restore its original shape when the clamp loosens thereabout or is removed therefrom (e.g., activated).

The bag 410 may be configured to be reversibly attached to the drainage container 402. As such, the first outlet 420 may include a sealing device that substantially prevents a fluid present in the first interior space 406 from flowing through the first outlet 420 when the bag 410 is detached from the drainage container 402. In an embodiment, the sealing device may be any of the sealing mechanisms disclosed herein (e.g., sealing device 156).

Figure 5:
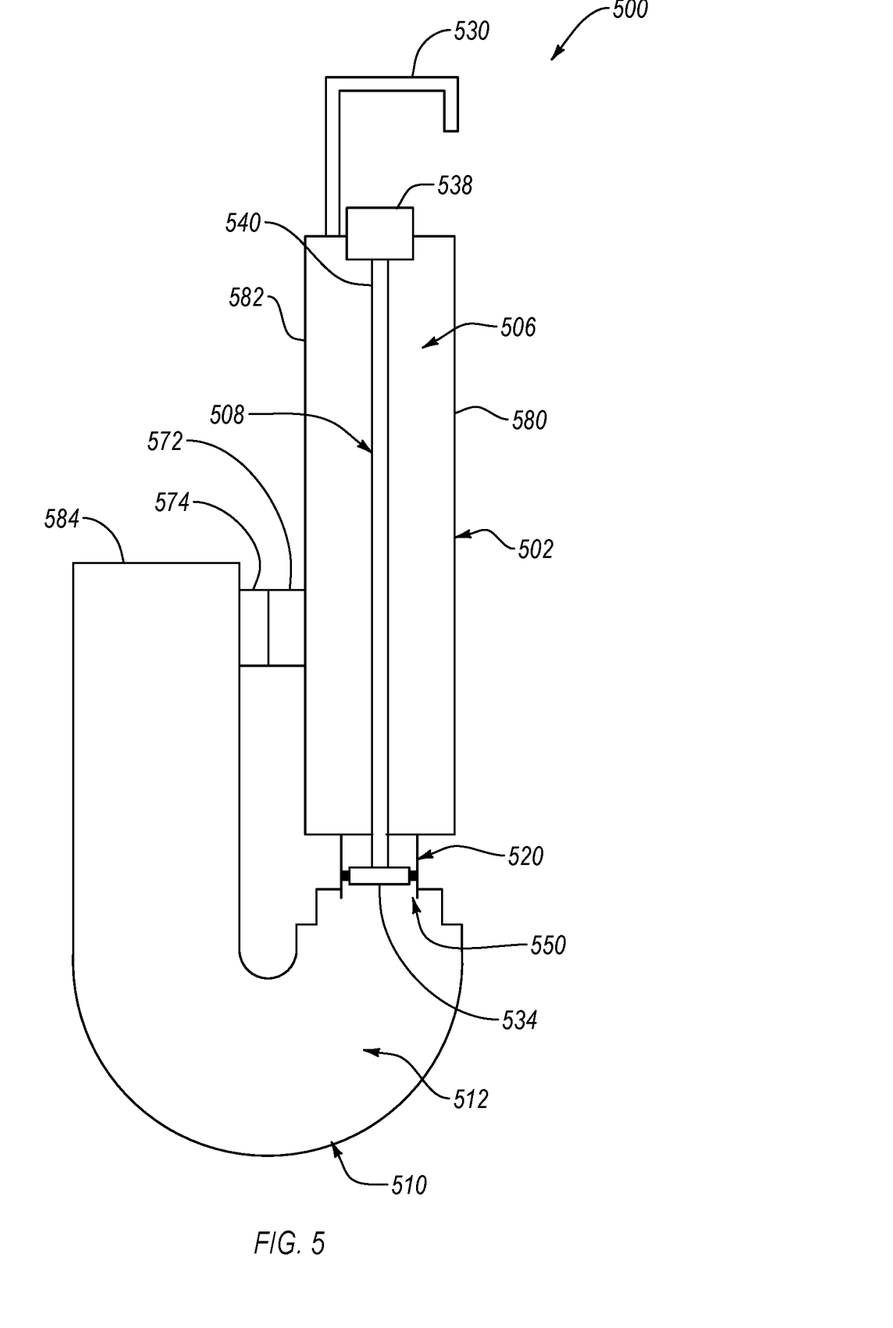
FIG. 5 is a schematic cutaway side view of a drainage bag system, according to an embodiment.

FIG. 5 is a schematic cutaway side view of a drainage bag system 500, according to an embodiment. The drainage bag system 500 is structurally similar to the drainage bag systems 100, 300, 400 shown in FIGS. 1, 3, and 4. Therefore, in the interest of brevity, an explanation of the components in both drainage bag systems 100, 300, 400, 500 that are identical or similar to each other will not be repeated unless the components function differently in the drainage bag systems 100, 300, 400, 500.

The drainage bag system 500 includes a drainage container 502 and a bag 510 connected to the drainage container 502. The drainage bag container 502 and the bag 510 may be formed from the same materials as the drainage container 102 and the bag 110, and the drainage container 502 may include one or more graduated markings thereon (not shown). The bag 510 is connected to the drainage container 502 such a vertical profile of the drainage bag system 500 is substantially minimized. The features illustrated in and described in relation to FIG. 5 may be used in any of the embodiments disclosed herein.

The drainage container 502 may include a front wall 580 and a back wall 582 that generally opposes the front wall 580. The drainage container 502 also includes a first outlet 520 formed at or near the bottommost portion of the drainage container 502. The first outlet 520 may fluidly couple a first interior space 506 of the drainage container 502 to a second interior space 512 of the bag 510. For example, the bag 510 may include a second inlet 550 that is fluidly coupled and reversibly attached to the first outlet 520 of the drainage container 502. The drainage bag system 500 may also include a fluid dispensing device 508 that is configured to selectively restrict or permit a fluid to flow from the first interior space 506 to the second interior space 512. The illustrated fluid dispensing device 508 may include a piston 534 and a manually-operable valve actuator 538 operably coupled to the piston 534 (e.g., using an elongated member 540). However, any fluid dispensing device disclosed herein may be used.

The bag 510 is connected to the drainage container 502 via the first outlet 520 and the second inlet 550. The bag 510 is also connected to the drainage container 502 using a first attachment device 572 coupled to the drainage container 502 and a second attachment device 574 coupled to the bag 510. The first attachment device 572 and the second attachment device 574 may include any of the attachment devices disclosed herein (e.g., the first attachment device 172 and/or the second attachment devices 174). In the illustrated embodiment, the first attachment device 572 may be coupled to the back wall 582 such that, when the first attachment device 572 is coupled to the second attachment device 574, a bottommost portion 584 (e.g., measured when the first attachment device 572 is not coupled to the second attachment device 574) of the bag 510 is positioned adjacent to the back wall 582. Additionally, the bottommost portion 584 of the bag 510 may be positioned above the second inlet 550 when the first attachment device 572 is coupled to the second attachment device 574 so that the second inlet 550 of the bag 510 is substantially aligned with the first outlet 520 of the drainage container 502. Connecting the first attachment device 572 to the second attachment device 574 may substantially minimize the vertical profile of the drainage bag system 500. For example, the bag 510 may be flexible to enable folding or bending the bag 510 to couple the second attachment device 574 to the first attachment device 572.

In an embodiment, the first attachment device 572 and the second attachment device 574 may be decoupled from each other when at least a portion of a fluid present in the first interior region 506 is emptied into the second interior region 512. For example, the first attachment device 572 may be operably coupled to the fluid dispensing device 508 such that activating the fluid dispensing device 508 also causes the first attachment device 572 to decouple from the second attachment device 574. For example, activating the fluid dispensing device 508 may pull the first attachment device 572 (e.g., a magnet) from the second attachment device 574. In an embodiment, the first attachment device 572 and the second attachment device 574 may be configured to decouple when the weight of the bag 510 exceeds a certain limit. In particular, at least partially filling the second interior space 512 may cause the cause the bag 510 to exceed to weight limit that forces the first attachment device 572 to decouple from the second attachment device 574. In an embodiment, a user of the drainage bag system 500 may manually decouple to the first attachment device 572 from the second detachment device 574. In an embodiment, the first attachment device 572 may decouple from the second detachment device 574 using any suitable method. In an embodiment, the first attachment device 572 and the second attachment device 574 may be configured to remain coupled when the at least a portion of a fluid present in the first interior region 506 is emptied into the second interior region 512. Such an embodiment may enable to the drainage bag system 500 to continuously maintain the low vertical profile of the drainage bag system 500.

In an embodiment, at least one of the first attachment device 572 or the second attachment device 574 may be omitted. For example, the back wall 582 may include a clamp configured to clasp a portion of the bag 510 (e.g., the bottommost portion 584) or the bag 510 may include a string configured (e.g., have sufficient length) to attached to a hook 530 or another component of the drainage bag system 500. In an embodiment, both the first attachment device 572 and the second attachment device 574 may be omitted. For example, the bag 510 may exhibit a side cross-sectional geometry configured to enable the drainage bag system 500 to exhibit a low vertical profile. For example, the bag 510 may exhibit a side cross-sectional geometry that is generally U-shaped, spiraled, or another suitable shape. The bag 510 may exhibit such a geometry even after the second interior space 512 is at least partially filled with a fluid or the weight of the fluid may cause the bag 510 exhibit a substantially planar side cross-sectional geometry.

While various aspects and embodiments have been disclosed herein, other aspects and embodiments are contemplated. The various aspects and embodiment disclosed herein are for purposes of illustration and are not intended to be limiting.

What is claimed:

1. A drainage bag system, comprising:
  a drainage container defining a first interior space configured to hold fluid therein, the drainage container further defining an outlet that allows access to the first interior space;
  a fluid dispensing device including a valve system that is configured to substantially prevent the fluid from flowing through the outlet when the fluid dispensing device is deactivated and permit the fluid to flow through the outlet when activated, the valve system including:

a piston configured to be moved from a first position to a second position, wherein at least a portion of the piston is disposed in the outlet when the piston is in at least the first position;

a manually-operable valve actuator operably coupled to the piston, the manually-operably valve actuator configured to move the piston from the first position to the second position; and an elongated member coupled to the piston and the manually-operable valve actuator; and a bag defining a second interior space configured to hold at least a portion of the fluid therein, the bag further defining an inlet, the inlet positioned and configured to be selectively fluidly coupleable to the outlet of the drainage container such that at least a portion of the fluid in the drainage container can be dispensed into the bag when the fluid dispensing device is activated.

2. The drainage bag system of claim 1, wherein the bag is flexible and disposable.

3. The drainage bag system of claim 1, wherein the piston substantially prevents the fluid from flowing through the outlet when in the first position and permits the fluid to flow through the outlet when in the second position.

4. The drainage bag system of claim 3, wherein the piston includes a seal.

5. The drainage bag system of claim 1, wherein at least a portion of the elongated member is hollow, the elongated member further including an inlet that fluidly couples the first interior space to the hollow portion of the elongated member.

6. The drainage bag system of claim 5, wherein the hollow portion of the elongated member extends from the inlet of the elongated member to a portion of the outlet that is not in fluid communication with the piston.

7. The drainage bag system of claim 1, wherein the outlet of the drainage container includes a flexible conduit, and wherein the valve system includes a clamp that collapses the flexible conduit when deactivated.

8. The drainage bag system of claim 1, wherein the valve system is at least partially positioned within the first interior space or attached to the drainage container.

9. The drainage bag system of claim 1, wherein the valve system is at least partially positioned within the second interior space or attached to the bag.

10. The drainage bag system of claim 1, wherein the drainage container includes a first attachment device spaced from the outlet and the bag includes a second attachment device spaced from the inlet, the first attachment device and the second attachment device are configured to be reversibly attached together.

11. The drainage bag system of claim 1, wherein the bag includes a sampling port formed in the bag, the sampling port configured to allow a syringe device to take at least one sample from the second interior space and to substantially prevent the fluid from flowing through the sampling port.

12. The drainage bag system of claim 1, wherein the bag includes a bottommost portion that is initially positioned adjacent to a back wall of the drainage container.

13. A method of operating a drainage bag system, the method comprising: filling at least a portion of a first interior space of a drainage container with a fluid; manipulating a manually-operable valve actuator of a fluid dispensing device to move a piston of the fluid dispensing device from a first position to a second position, thereby selectively permitting the fluid to flow from the first interior space through and out of an outlet of the drainage container, wherein the fluid dispensing device includes an elongated member coupled to the piston and the manually-operable valve actuator, and wherein at least a portion of the piston is disposed in the outlet of the drainage container when the piston is in at least the first position; and responsive to manipulating the manually-operable valve actuator of the fluid dispensing device, filling at least a portion of a second interior space of a bag fluidly coupled to the drainage container with the fluid that is flows through and out of the owlet of the drainage container.

14. The method of claim 13, further comprising, after filling at least a portion of the second interior space with the fluid, selectively deactivating the fluid dispense device to prevent the fluid to flow from the first interior space through and out of the outlet of the drainage container.

15. The method of claim 14, wherein selectively deactivating the fluid dispense device includes manipulating the manually-operable valve actuator of the fluid dispensing device.

16. The method of claim 14, wherein selectively deactivating the fluid dispense device includes ceasing to manipulate the manually-operable valve actuator of the fluid dispensing device.

17. The method of claim 13, further comprising fluidly decoupling the outlet from an inlet.

18. The method of claim 17, further comprising, after fluidly decoupling the outlet from the inlet, fluidly coupling a new bag to the drainage container.

19. A drainage bag system, comprising:

a drainage container defining a first interior space configured to hold fluid therein, the drainage container further defining an outlet that allows access to the first interior space, the drainage container including a first attachment device;

a fluid dispensing device including a valve system at least partially disposed within the first interior space, the valve system including:

a piston configured to be moved from a first position to a second position, the piston substantially prevents the fluid from flowing through the outlet when in the first position and permits the fluid to flow through the outlet when in the second position;

a manually-operable valve actuator operably coupled to the piston, wherein the manually-operable valve actuator configured to move the piston from the first position to the second position; and an elongated member extending from the piston to the manually-operable valve actuator, wherein at least a portion of the elongated member is hollow, the elongated member further including an inlet that fluidly couples the first interior space to the hollow portion of the elongated member, wherein the hollow portion of the elongated member extends from the inlet of the elongated member to a portion of the outlet that is not in fluid communication with the piston; and a bag defining a second interior space configured to hold at least a portion of the fluid therein, the bag further defining an inlet, the inlet positioned and configured to be selectively fluidly coupleable to the outlet of the drainage container such that at least a portion of the fluid in the drainage container can be dispensed into the bag when the fluid dispensing device is activated, the bag including a second attachment device that is configured to be reversibly attached to the first attachment device.

* * * * *